Figure 6:
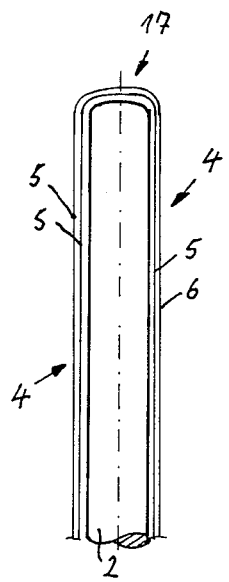

United States Patent [19]

Franke

[11] Patent Number: 4,870,365

[45] Date of Patent: Sep. 26, 1989

[54] MEASURING DEVICE, REINFORCEMENT ROD, PROCESS FOR DETECTING MECHANICAL DEFECTS IN FIBER COMPOSITE BUILDING ELEMENTS AND APPLICATION OF THE PROCESS

[76] Inventor: Lutz Franke, Muehlenweg 143, D-2105 Seevetal 2, Fed. Rep. of Germany

[21] Appl. No.: 113,185

[22] PCT Filed: Dec. 19, 1986

[86] PCT No.: PCT/EP86/00768

§ 371 Date: Sep. 2, 1987

§ 102(e) Date: Sep. 2, 1987

[87] PCT Pub. No.: WO87/04209

PCT Pub. Date: Jul. 16, 1987

[30] Foreign Application Priority Data

Jan. 3, 1986 [DE] Fed. Rep. of Germany ....... 3600034

[51] Int. Cl.$^4$ ............................................. G01R 31/08
[52] U.S. Cl. ................................... 324/512; 324/519; 324/522; 324/525; 324/61 R; 324/65 R; 340/604
[58] Field of Search ............... 324/512, 519, 522, 523, 324/525, 61 R, 65 R; 340/602, 604, 605; 73/73, 74, 799; 428/378, 375, 379, 373; 174/11 R

[56] References Cited

U.S. PATENT DOCUMENTS

| | | | |
|---|---|---|---|
| 293,775 | 2/1884 | Patterson | 174/11 R |
| 539,939 | 5/1895 | Gharky | 324/512 |
| 4,265,981 | 5/1981 | Campbell | 428/373 |
| 4,348,635 | 9/1982 | Wright et al. | 324/61 R |
| 4,480,251 | 10/1984 | McNaughton et al. | 340/604 |

FOREIGN PATENT DOCUMENTS 56317 6/1968 Luxembourg .
2152088 7/1985 United Kingdom .

Primary Examiner—Reinhard J. Eisenzopf
Assistant Examiner—Anthony L. Miele
Attorney, Agent, or Firm—Sixbey, Friedman, Leedom & Ferguson

[57] ABSTRACT

At least a pair (4) or a band of wires of an electrically conducting material is longitudinally embedded in the fiber composite material forming the building element (2) and firmly secured to the fiber composite material over the whole length of the wires. A weak current source (7) is connected to the free ends of the wires. The current conduction is then monitored, the capacitance is measured or the current conduction and the capacitance are measured.

4 Claims, 2 Drawing Sheets

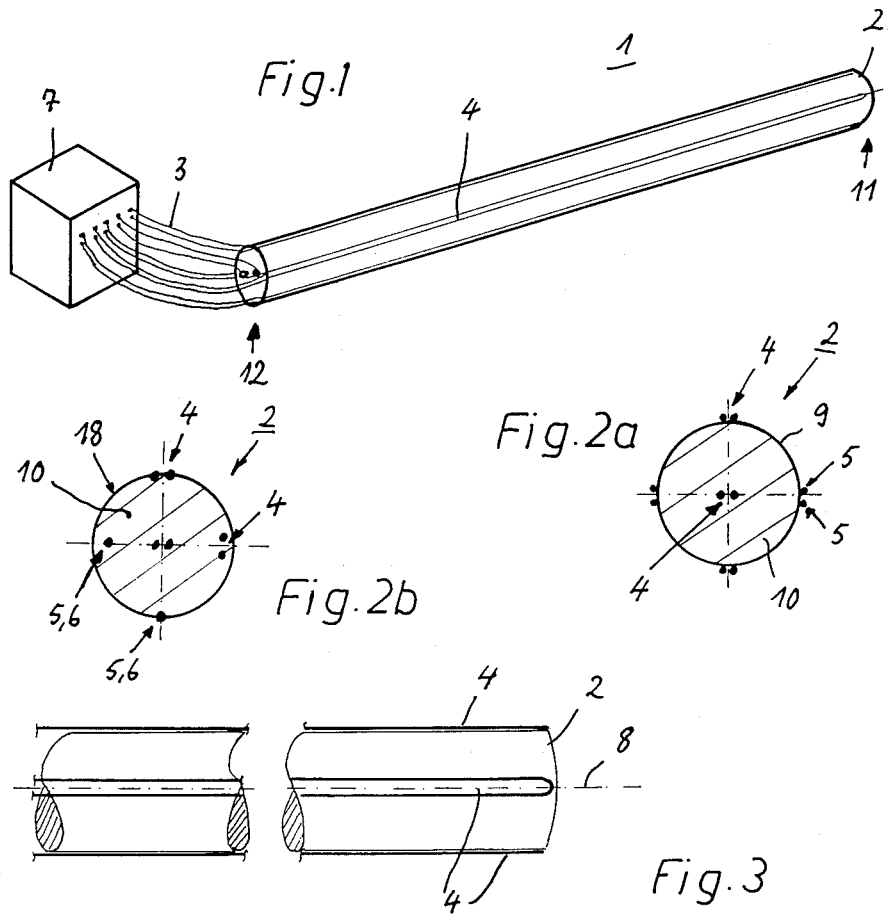
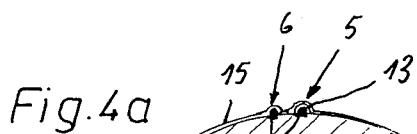
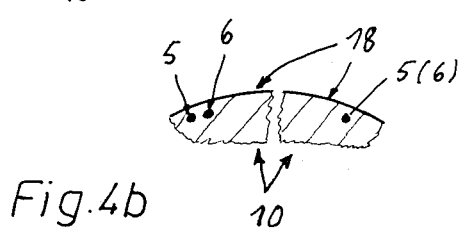

MEASURING DEVICE, REINFORCEMENT ROD, PROCESS FOR DETECTING MECHANICAL DEFECTS IN FIBER COMPOSITE BUILDING ELEMENTS AND APPLICATION OF THE PROCESS

The invention relates to a process for detection of mechanical defects at structural members being of fiber composite, the application of the process as well as a measuring device and an armour bar for realization the process.

E.g. for prestressed concrete construction it is known to use individual or bunches of armour bars and load-bearing fixtures being of fiber composite. The problem with such armour bars is that damages, breaks, and water effects cannot be detected, especially if the armour bars are not accessible after assembling. This can be the case with bunches of armour bars for prestressed concrete construction, pressed after stressing. In such bunches breaks of individual bars are not recognizable at the bunch end and the bunch anchorage respectively, and therefore breaks cannot be detected by common monitoring systems. Buch such defects reduce the safety of a constructional part. Only with a higher and possibly critical number of breaks in larger bunches the constructional part shows external reactions, e.g. as increased deflections or cracks. It is further not possible to find out a locally restricted water effect at highly stressed fiber composite bars, what is a special disadvantage. Such a water intake effect can result in a deterioration of highly stressed armour bars.

It is the purpose of the invention to show a process and an arrangement for realization of the process for an easy and simple detection of defects in armour bars and load-bearing fixtures of fiber composite with respect to their position.

According to the invention the problem is solved in that at least one pair of wires, fibers, bunch of fibers or bands of conductive material is lenghwise inserted in the fiber composite of the structural member and firmly joined with the fiber composite of full wire, fiber or band length, and that a source of weak-current is connected to the free wire fiber, or band ends and either the current conduction or the capacity is determined or the current conduction and the capacity are determined.

Further features of the invention in respect of the application of the process, the measuring device, and the armour bar for working of the process are described in the subclaims and illustrated below with reference to the drawings. It shows FIG. 1 a measuring device with an armour bar in a schematic diagrammatic view, FIG. 2a an armour bar in a cross-sectional view FIG. 2b a general arrangement of further contructions of an armour bar in a cross-sectional view, FIG. 3 an armour bar in a diagrammatic to view, FIG. 4a the arrangement of a pair of wires on the surface of an armour bar in an enlarged detail view, FIG. 4b the arrangement of a single wire, a fiber or a bunch of fibers in the rim zone of an armour bar in an enlarged detail view, FIG. 5 an armour bar with lengthwise graduated arranged pairs of wires in a diagrammatic figuration, FIG. 6 an armour bar with a pair of wires constructed as a loop in a diagrammatic figuration, FIG. 7 an armour bar with bands of wires arranged on the surface in a cross-sectional view.

The measuring device for detection of damages or breaks as well as water inlet effects at inaccessibly installed armour bars 2 of fiber composite is constructed as a sensor bar as well as a measuring instrument 7. The sensor bar is a common armour bar 2 with a pair 4 of wires 5, 6 inserted lenghtwise in the core 10 at bar production, e.g. at drawing from nozzles. Instead of the wires 5, 6 also bands, fibers, bunches of fibers, or conducting rovings e.g. made of glass fibers can be used. Further pairs 4 of wires 5, 6 or individual wires can be arranged in the rim zone of the cross-section or on the surface 9 of the armour bar 2 spaced apart (FIG. 1). In FIG. 2a and 2b respectively an armour bar 2 is shown diagrammatically in a cross-sectional view. In FIG. 2a pairs 4 of wires 4, 6 are arranged on the surface 9 of the armour bar 2. In the center of the core 10 a pair 4 of wires 5, 6 is also provided. FIG. 2b shows varations concerning the arrangement of pairs 4 of wires 5, 6 and individual wires 5, 6 respectively. Therefore it is possible, to arrange the pairs 4 of wires 5, 6 also in the rim zone 18 of the armour bar 2 or under the rim zone 18 in the region of the core 10. Further individual wires 5, 6 can be provided, inserted on the rim zone 18, under the rim zone 18, or in the region of the rim zone 18 of the armour bar. At one bar end 11 the wires 5, 6 of the pairs 4 of wires are electroconductively connected. For assembling of the armour bar 2 into the constructional part bar end 11 is arranged at the not or less accessible section. The wires 5, 6 preferably consist of a noncorrosive material, e.g. a copper base alloy. Their thickness usually is 0.1 to 0.5 mm. If not insulated wires are used, the space between the wires should be at least 1 mm. The insulation 13 of the wires 5 must be firmly joined with the surface of the wires, not to prevent the separation of the wire 5 with the insulation 13 in case of a break of the armour bar. In order to get a plane connection between the wires 5, 6 and the surface of the armour bar 2, the wires 5, 6 are connected with the armour bar 2 over the whole length by means of a bonding agent. It is possible to put a protective covering 15 around the armour bar 2 with the wires 5, 6 arranged at the surface 9 and fasten it at the surface 9 of the armour bar 2 (FIG. 4a). In FIG. 4b it is diagrammatically shown that the pair 4 of wires 5, 6 or individual wires 5, 6 under the rim zone 18 can be inserted in the core 10 of the armour bar 2.

By means of the measuring device 1 it is possible to carry out different measuring processes at the armour bar. A bar break or several breaks of cross-sectional parts can be detected by means of a source of weak current in connection with an indicator lamp or an ammeter. The measuring instrument 7 is connected to the wires 5, 6 of the pairs 4 of wires by means of the joining pieces 3 and the current conduction is controlled. An interruption of the current conduction is a proof for a break of a wire of the specific pair 4 of wires and therefore also a proof for a break in the amour bar 2.

In order to localize the exact position of the break relative to the bar end 12, the measuring instrument 7 is a capacitance measuring instrument. This principle of measurement is based on the dependence of the condensor capacity on its area and the knowledge that also parallelly arranged and insulated wires operate like condensors. For application of a capacitance measuring instrument it is necessary that the wires 5 of a pair 4 of wires to be checked are parallelly arranged at a constant distance at the armour bar 2. If the armour bar 2 and one of the wires 6 tears, the break can be localized from the changing capacity. It was found that there is a linear relation between the length of the armour bar 2 and the capacity. For detection of breaks it is necessary that in case of a local delamination of the armour bar 2 the inserted wire 5, 6; 6, 6; 5, 5 of a pair 4 of wires can't release from the resin matrix along the bar in the break area, otherwise the wires would adjust the extension by means of elongation and they would not be divided. In this case a detection of the break by measurement techniques would not be possible.

With the measuring device 1 the average elongation of an armour bar 2 and the effective elongation of rectilinearly stressed armour bars 2, respectively, can also be determined by means of a change of resistance of an integrated wire coil, constructed as a pair 4 of wires 5, 5; 5, 6; 6,6. The correlation between the change of resistance and the elongation of the armour bar 2 can be determined by means of a calibration of a standarized bar length.

Figure 5:
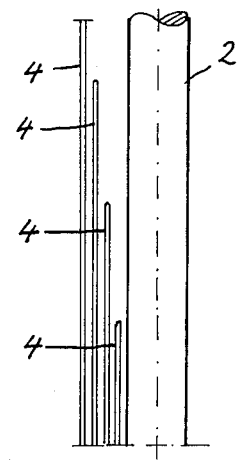

Armour bars 2 of fiber composite can be damaged by water effect and the chance of breaks is especially increased. It is possible to determine the water effect on the armour bar 2 by means of the measuring device 1. The effect of water on the armour bar 2 can be determined by measuring the change of resistance within the range from infinite to zero as well as by change in capacity. For this the pairs 4 of wires are arranged at the surface 9 of the armour bar 2, in which one wire 6 is not insulated. The wires 5, 6; 6, 6 and or pairs 4 of wires can also be arranged along the armour bar 2 graduated by length (FIG. 5). A water intake at the armour bar 2 can easily be localized by measuring individual pairs 4 of wires. A water intake is then localized before the end section of that pair 4 of wires, which has been measured at last and which has an infinite capacity. It is also possible to have a pair 4 of wires 5, 5; 6, 6 connected to a loop 17, surrounding the whole armour bar lengthwise. Pairs 4 of wires 5, 6; 6, 6 arranged in the core 10 of the armour bar can also be connected to the loop 17. In case of a water effect to the armour bar 2 the changes in resistance may be different at the end sections of the pair 4 of wires, because of the location of the penetration of moisture. The location of the penetration of moisture can be determined by these different resistance values (FIG. 6).

Figure 7:
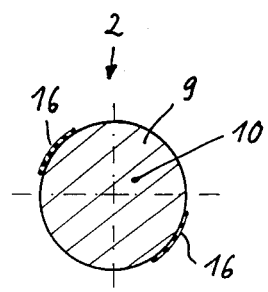

Instead of individual pairs 4 of wires 5, 6; 6, 6 fibers, bunches of fibers, electroconductive rovings like glass fiber rovings or bands 16 of wires can be used, arranged at the surface 9 of the armour bar 2 (FIG. 7). The pairs 4 of wires 4 as well as the bands 16 can consist of non-corrosive metallic material, e.g. the already mentioned copper base alloys, as well as nonmetallic materials such as carbon compounds. In the latter case the bands 16 can be made of carbon fibers, resulting in an extreme high electrical resistance. These bands 16 are specialized for localization of penetration of moisture at the armour bar 2.

The measuring device 1 with the measuring system is not only used for armour bars 2 and bunches of armour bars 2 accessible only from one side. Application is also possible with completely enclosed armour bars 2 or bunches of armour bars. In this case a control cable is provided, connected to the joining piece 3 of the armour bars 2 and laid outwards through the outer case. It is also possible to place the joining pieces 3 outwards the contructional part to connect them to the control cable outside. Furthermore it is possible to use the measuring device 1 with the measuring process for inaccessible armour-clamps or inaccessible constructions in the ground.

I claim:

1. Process for simultaneous precise detection of the position of mechanical defects at a surface or breaks and water effects, as well as for determining the elongation of a rectilinearly stressed, especially inaccessibly installed, structural member in the nature of armour bars and bar-like loadbearing fixtures, the structural member being made of a fiber composite material with electrical measuring elements having mechanical properties approximating those of the fiber composite material inserted lengthwise into the fiber composite material of the structural member and firmly joined with the fiber composite along the full length of the structural member, wherein at least one measuring element is inserted in a core of the structural member and at least one measuring element is fixed at the surface of the structural member, parallel to each other, the measuring elements being selected from the group consisting of wires, conductive fibers, bunches of conductive fibers or bands, wherein said measuring elements comprise at least one insulated wire and at least one uninsulated wire, and then a source of weak current and a measuring device is connected to one end of the measuring elements, and electrical capacity measured via said one end of the measuring elements in a manner eliminating need for an electrical connection at an opposite end of the structural member.

2. Process according to claim 1, wherein the measuring elements inserted comprise a bunch of fibers formed of single conductive glass fiber rovings.

3. Process according to claim 1, wherein bands with high electrical resistance are bonded on the surface of the armour bar or load-bearing fixture.

4. Bar-like structural element of fiber composite, with an electroconductive band-like capacitive measuring element within a core thereof, wherein said measuring element is arranged in the core of the structural element parallel to a longitudinal axis thereof; wherein the said measuring element comprises wires joined to each other by a covering of insulation firmly affixed thereover and emerges from the fiber composite of the structural element at one end and a control cable is connected thereto, while the measuring element is free of electrical connections at the other end of the structural element, and wherein another measuring element is affixed at a surface of the structural member and comprises at least one insulated wire and at least one uninsulated wire, the measuring elements being parallel to each other.

* * * * *